United States Patent
Appeaning et al.

(10) Patent No.: US 9,480,760 B2
(45) Date of Patent: Nov. 1, 2016

(54) LIGHT-ACTIVATED ANTIMICROBIAL ARTICLE AND METHOD OF USE

(75) Inventors: Maria A. Appeaning, St. Paul, MN (US); Audrey A. Sherman, St. Paul, MN (US); Michael A. Meis, Stillwater, MN (US); Marie A. Boulos, West St. Paul, MN (US); Kevin D. Landgrebe, Woodbury, MN (US); Kevin R. Schaffer, Woodbury, MN (US); Matthew T. Scholz, Woodbury, MN (US); Thu-Van T. Tran, Maplewood, MN (US); Narina Y. Stepanova, Inver Grove Heights, MN (US); Caroline M. Ylitalo, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/379,573

(22) PCT Filed: Jun. 23, 2010

(86) PCT No.: PCT/US2010/039577
§ 371 (c)(1),
(2), (4) Date: Dec. 20, 2011

(87) PCT Pub. No.: WO2010/151563
PCT Pub. Date: Dec. 29, 2010

(65) Prior Publication Data
US 2012/0100039 A1    Apr. 26, 2012

Related U.S. Application Data

(60) Provisional application No. 61/220,505, filed on Jun. 25, 2009.

(51) Int. Cl.
*A61L 2/10* (2006.01)
*A61L 2/08* (2006.01)

(52) U.S. Cl.
CPC .................... *A61L 2/088* (2013.01)

(58) Field of Classification Search
CPC .................... A61L 2/088; A61L 2/10
USPC ................................. 422/22, 24
See application file for complete search history.

(56) References Cited

U.S. PATENT DOCUMENTS

| 4,310,509 A | 1/1982 | Berglund |
| 4,584,192 A | 4/1986 | Dell |

(Continued)

FOREIGN PATENT DOCUMENTS

| CA | 1038135 | 9/1978 |
| CN | 1771073 | 5/2006 |

(Continued)

OTHER PUBLICATIONS

English Translation of JP2002186861—Tougeta et al., Porous Photocatalyst and Method for Manufacturing the Same, Feb. 7, 2002, JPO, Pertinent Pages: Abstract*

(Continued)

*Primary Examiner* — Sean E Conley
*Assistant Examiner* — Donald Spamer
(74) *Attorney, Agent, or Firm* — Qiang Han

(57) ABSTRACT

Light-activated antimicrobial devices and articles are disclosed. The devices include a light source and a light-activated antimicrobial article comprising a photosensitizer and a viscoelastic material such as a pressure sensitive adhesive adapted to receive light from the light source. The viscoelastic material may be adapted to transport light by total internal reflection. The photosensitizer may comprise a dye, a metal oxide or a composition that comprises anions that oxidize or react to form a gas. Upon activation of the light source, the photosensitizer absorbs light from the light source such that antimicrobial activity is exhibited. The photosensitizer may be included in the light-activated antimicrobial article or it may be provided as a topical composition that is separate from the article. The light-activated antimicrobial articles and devices may have constructions similar to those of wound dressings.

21 Claims, 3 Drawing Sheets

(56) References Cited

U.S. PATENT DOCUMENTS

| | | | |
|---|---|---|---|
| 5,160,328 A * | 11/1992 | Cartmell et al. | 604/307 |
| 5,198,922 A * | 3/1993 | Chahroudi | 359/290 |
| 5,690,863 A * | 11/1997 | Schuman | 252/582 |
| 5,738,642 A | 4/1998 | Heinecke | |
| 5,803,086 A | 9/1998 | Scholz | |
| 5,830,526 A | 11/1998 | Wilson | |
| 5,979,450 A | 11/1999 | Baker | |
| 5,985,395 A | 11/1999 | Comstock | |
| 6,096,066 A | 8/2000 | Chen | |
| 6,174,399 B1 * | 1/2001 | DeCandia et al. | 156/229 |
| 6,248,733 B1 | 6/2001 | Landgrebe | |
| 6,264,976 B1 | 7/2001 | Heinecke | |
| 6,288,172 B1 | 9/2001 | Goetz | |
| 6,379,016 B1 | 4/2002 | Boyd | |
| 6,432,396 B1 | 8/2002 | Landgrebe | |
| 6,790,409 B1 * | 9/2004 | Nakamura et al. | 422/22 |
| 6,890,553 B1 * | 5/2005 | Sun et al. | 424/449 |
| 7,223,270 B2 | 5/2007 | Altshuler | |
| 7,223,281 B2 | 5/2007 | Altshuler | |
| 7,329,273 B2 | 2/2008 | Altshuler | |
| 7,329,274 B2 | 2/2008 | Altshuler | |
| 7,354,448 B2 | 4/2008 | Altshuler | |
| 7,402,722 B2 | 7/2008 | Hill | |
| 7,422,598 B2 | 9/2008 | Altshuler | |
| 2003/0170308 A1 * | 9/2003 | Cleary et al. | 424/486 |
| 2003/0228459 A1 | 12/2003 | Mrozinski | |
| 2004/0147984 A1 | 7/2004 | Altshuler | |
| 2005/0058821 A1 | 3/2005 | Smith | |
| 2005/0070976 A1 | 3/2005 | Samuel | |
| 2006/0035039 A1 | 2/2006 | Ylitalo | |
| 2006/0148915 A1 | 7/2006 | Floyd | |
| 2006/0173514 A1 * | 8/2006 | Biel et al. | 607/88 |
| 2007/0009582 A1 * | 1/2007 | Madsen et al. | 424/445 |
| 2007/0232486 A1 * | 10/2007 | Aso | A61L 9/18 502/208 |
| 2007/0238660 A1 | 10/2007 | Michielsen | |
| 2007/0239232 A1 * | 10/2007 | Kurtz et al. | 607/87 |
| 2007/0278109 A1 * | 12/2007 | Kendig et al. | 205/709 |
| 2008/0057811 A1 * | 3/2008 | Yahiaoui et al. | 442/154 |
| 2008/0226748 A1 * | 9/2008 | Stevenson | 424/665 |
| 2009/0105437 A1 | 4/2009 | Determan | |
| 2010/0048804 A1 | 2/2010 | Determan | |

FOREIGN PATENT DOCUMENTS

| | | | |
|---|---|---|---|
| CN | 1901968 | 1/2007 | |
| JP | 2002186861 | * 2/2002 | B01J 37/02 |
| JP | 2003-116907 | 4/2003 | |
| JP | 2004-242705 | 9/2004 | |
| TW | 548130 | 8/2003 | |
| WO | WO 94-02022 | 2/1994 | |
| WO | WO 99-62822 | 12/1999 | |
| WO | 00/25940 | 5/2000 | |
| WO | WO 03-037504 | 5/2003 | |
| WO | WO 03/058301 | 7/2003 | |
| WO | WO 2007/059226 | * 11/2006 | A61K 31/39 |
| WO | WO 2007-127894 | 11/2007 | |
| WO | WO 2008/017975 | 2/2008 | |
| WO | WO 2009-048743 | 4/2009 | |
| WO | WO 2010-005655 | 1/2010 | |
| WO | WO 2010-017087 | 2/2010 | |
| WO | WO 2011-008441 | 1/2011 | |
| WO | WO 2011-022525 | 2/2011 | |

OTHER PUBLICATIONS

Bezman, "Photodynamic Inactivation of *E. Coli* by Rose Bengal Immobilized on Polystyrene Beads", Photochemistry and Photobiology, 1978, vol. 28, pp. 325-329.

Lenard, "Photoinactivation of Influenza Virus Fusion and Infectivity by Rose Bengal", Photochemistry and Photobiology, 1993, vol. 58, No. 4, pp. 527-531.

"OLED 'light bandage' helps in treatment of skin cancer," *LEDs Magazine*, Nov. 2, 2006, 2 pages.

International Search Report for PCT/US2010/039577, mailed Dec. 7, 2010, 5 pages.

* cited by examiner

LIGHT-ACTIVATED ANTIMICROBIAL ARTICLE AND METHOD OF USE

CROSS REFERENCE TO RELATED APPLICATIONS

This application is a national stage filing under 35 U.S.C. 371 of PCT/US2010/039577, filed on Jun. 23, 2010, which claims priority to U.S. Provisional Application No. 61/220,505, filed on Jun. 25, 2009, the disclosure of which is incorporated by reference in its/their entirety herein.

FIELD

This disclosure relates to microbiology, particularly to antimicrobial articles, devices and methods of use. Antimicrobial activity is induced by providing light to a photosensitizer.

BACKGROUND

Infectious diseases often result from invasion of the body by pathogenic microorganisms including bacteria, fungi and viruses. Over the years, many chemistries and methods have been developed to kill or inhibit the growth of pathogenic microorganisms including the development and use of antibiotics, antiviral agents and oxidizing agents. Electromagnetic radiation in many wavelength ranges has also been used. It is known that pathogenic microorganisms may be killed or their growth inhibited by exposure of the microorganisms to light in the presence of oxygen and certain photosensitizers.

SUMMARY

Light-activated antimicrobial devices and articles are disclosed. The devices may include a light source, and a light-activated antimicrobial article comprising a photosensitizer and a viscoelastic material adapted to receive light from the light source. The viscoelastic material may be adapted to transport light by total internal reflection. The photosensitizer may be incorporated into the viscoelastic material, or it may be part of a photosensitive layer disposed on the viscoelastic material. The photosensitizer may comprise a dye, a metal oxide or a composition that comprises anions that oxidize or react to form a gas. Useful viscoelastic materials include pressure sensitive adhesives. The light-activated antimicrobial devices may have a construction similar to that of a wound dressing, wherein the viscoelastic material is, e.g., disposed on a film backing such as an elastic film backing.

The light-activated antimicrobial articles and devices may be used as part of a method for inhibiting the growth of microorganisms. A suitable method may comprise: providing a light source, providing a light-activated antimicrobial article comprising a photosensitizer and a viscoelastic material adapted to receive light from the light source, and coupling the light source and the photosensitizer such that the photosensitizer absorbs light from the viscoelastic material. Coupling the light source and the photosensitizer may comprise contacting the light source and the viscoelastic material. The light-activated antimicrobial article may be applied to the skin of a patient before or after the light source is coupled with the photosensitizer. The light-activated antimicrobial article may be exposed to a surface having a microorganism disposed thereon. The method may comprise activating the light source such that it emits light that is absorbed by the photosensitizer.

Another suitable method may comprise: providing a light source, providing a viscoelastic material adapted to receive light from the light source, applying a topical composition to the skin of a patient, the topical composition comprising a photosensitizer that absorbs light that is received by the viscoelastic material, contacting the topical composition on the skin of the patient with the viscoelastic material, and coupling the light source and the photosensitizer such that the photosensitizer absorbs light from the viscoelastic material.

These and other aspects of the invention are described in more detail below. The above summary is not intended to limit the claimed subject matter in any way.

BRIEF DESCRIPTION OF DRAWINGS

The figures are schematic drawings of exemplary light-activated antimicrobial articles and devices that are disclosed herein. The articles and devices are not necessarily drawn to scale.

DETAILED DESCRIPTION

Figure 1A:
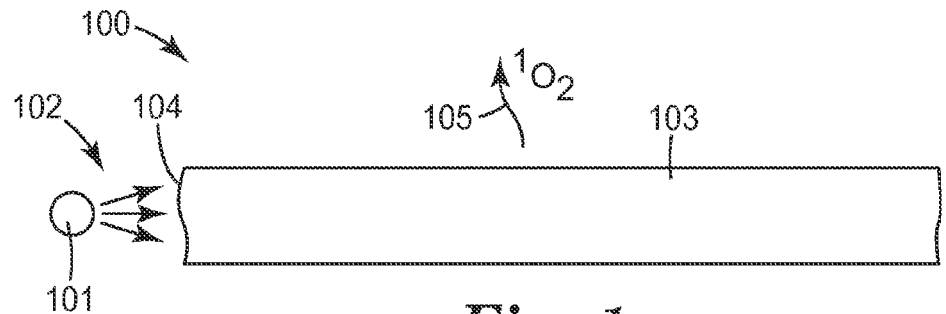
FIGS. 1a, 1b, 2 and 3 are schematic cross sections of exemplary light-activated antimicrobial devices.

This disclosure relates to U.S. Provisional Application No. 61/079,639 filed on Jul. 10, 2008 (Sherman et al.); 61/087,387 filed on Aug. 8, 2008 (Sherman et al.); 61/114,865 filed on Nov. 14, 2008 (Sherman et al.); 61/114,849 filed on Nov. 14, 2008 (Sherman et al.); and 61/169,973 (Sherman et al.), filed on Apr. 16, 2009, all incorporated herein by reference.

Singlet oxygen is generated in neutrophils and macrophages for use in killing microorganisms. Superoxide dismutases, catalases, and peroxidases are defenses against radical- and reduced-oxygen species, but are not effective against singlet oxygen. A few microorganisms, such as Cercospora, are inherently resistant to singlet oxygen, and Gram-positive bacteria are generally more easily killed by singlet oxygen than Gram-negative bacteria. Enveloped viruses are inactivated by singlet oxygen more readily than nonenveloped viruses. It is notable that not a single documented case of acquired resistance by a bacterium, fungus, or virus to singlet oxygen is known.

The "photodynamic effect" is a term used to describe destruction of cells and microbes by photosensitizers in the presence of light. Under conditions where oxygen concentration is high and there are no reducing agents present, singlet oxygen is believed to be the destructive agent. This is the predominant mechanism (the so-called Type II mechanism) for cell destruction in cases where the photosensitizer cannot enter the cell. The Type II mechanism is known to be the predominant means of phototoxicity to *Escherichia coli* for the xanthene dyes, such as rose bengal, for example, which upon irradiation generates reactive oxygen species such as singlet oxygen and superoxide radical anion. For photosensitizers that can pass through the lipid bilayer membrane into the interior of the cell where reducing agent concentrations, such as NADPH and glutathione, are high, the so-called Type I mechanism has been determined to be the predominant one leading to cell destruction. This mechanism involves, ultimately, the formation of a photosensitizer free radical and reactive oxygen species such as hydrogen peroxide, hydroxyl radical, and superoxide radical anion.

Some effort has been directed toward utilization of photosensitizers in free form (e.g., phthalocyanine, porphyrin, hypericin, and rose bengal) for killing bacteria and fungi and for inactivating viruses. For example, photoinactivation of influenza virus by rose bengal and light was disclosed by Lenard et al. in *Photochemistry and Photobiology*, 58, 527-531 (1993). Also, WO 94/02022 (Rabone et al.) discloses improved germicidal compositions utilizing rose bengal in photodynamic killing of microorganisms on surfaces.

Effort has also been directed toward utilization of photosensitizers in bound form in which they are relatively immobilized as compared to the free form. Photosensitizers have been covalently or ionically bonded to beads, larger molecules, oligomers, macromolecules and polymers. For example, an ionic binder was used to bind dye to woven and nonwoven fabrics as disclosed in U.S. Pat. No. 5,830,526 (Wilson et al.). Positively charged polymer carrier was used to ionically bond rose bengal such that microbes were killed in the presence of oxygen and light. Photodynamic inactivation of *Escherichia coli* by rose bengal bonded to polystyrene beads was disclosed by Bezman et al. in *Photochemistry and Photobiology*, 28, 325-329, (1978).

Disclosed herein are light-activated antimicrobial articles, devices and methods of using the articles and devices. "Light-activated" refers to the ability of an article, device or method to induce a photodynamic effect. In this sense, light-activated means that a photosensitizer is present and transfers energy from light to generate reactive species such as singlet oxygen, hydrogen peroxide, hydroxyl radical, superoxide radical anion, photosensitizer radical and many other radicals that may be formed depending upon the particular environment of the photosensitizer. Preferred photosensitizers produce singlet oxygen, hydrogen peroxide, hydroxyl radical, and/or superoxide radical anion without producing any toxic by-products. Thus, the articles, devices and methods disclosed herein are also "light-activated" in the sense that they can become antimicrobial when subjected to light.

"Antimicrobial" refers to the ability of an article, device or method to kill or inhibit the growth of microorganisms such as bacteria, fungi and viruses. To "kill or inhibit the growth of includes limiting the presence of at least one virus, at least one bacterium, at least one fungus, or a combination thereof. To" kill or inhibit the growth of also includes inactivation and prevention of the replication of or reducing the number of a microorganism. Different terms may be used for different microorganisms.

An article is considered to be "light-activated antimicrobial" if the article can be optically coupled to a light source such that when the light source is turned on to emit light, the article kills or inhibits the growth of some affected microorganism. Various incubation and testing methods can be used to determine the number of colony forming units per sample of an affected microorganism. The number of colony forming units killed or inhibited by the article can be determined by subjecting separate samples to light with and without the article, as long as the same or nearly the same incubation and testing methods are used. "Light-activated antimicrobial" articles result in a decrease in colony forming units, for example, in an amount of from about 80 to 100%, or from about 90 to 99.99%. Antimicrobial activity on textiles may be determined using AATCC Test Method 100.

A device is considered to be "light-activated antimicrobial" if the device comprises a light source optically coupled to a light-activated antimicrobial article such that when the light source is turned on to emit light, the device kills or inhibits the growth of some affected microorganism (as described above for the article).

A method is considered to be "light-activated antimicrobial" if the method involves some use of the light-activated antimicrobial article and/or the device to kill or inhibit the growth of some affected microorganism (as described above for the article).

Affected microorganisms include DNA viruses, RNA viruses, RNA retroviruses, Gram-negative bacteria, Gram-positive bacteria and fungi. Affected microorganisms also include single- and double-stranded nucleic acid genomes. Affected microorganisms include negative single-stranded RNA genomes such as Orthomyxoviridae, Rhabdoviridae, Paramyxoviridae, Bunyaviridae, and Filoviridae. These are enveloped viruses. Orthomyxoviridae include the influenza viruses A, B, and C. Rhabdoviridae include rabies virus and vesicular stomatitis virus. Paramyxoviridae include parainfluenza virus of mammals (including mumps virus) and pneumovirus (such as respiratory syncytial viruses of man and cattle). Bunyaviridae include hantavirus, which causes Korean hemorrhagic fever and hantavirus pulmonary syndrome. Filoviridae include Marburg virus and Ebola virus.

Affected microorganisms include positive single-stranded RNA genomes such as Picornaviridae (non-enveloped), Retroviridae, and Togaviridae. Picornaviridae include polioviruses, coxsackieviruses, hepatitis A virus, and rhinovirus. Retroviridae include, for example, human immunodeficiency virus (HIV), simian immunodeficiency virus (SIV), and equine infectious anemia virus (EIAV). Togaviridae include Semliki Forest virus, yellow fever virus, Dengue virus, tick-borne virus, and rubella virus. Parvovirus (non-enveloped) is the only virus having a single-stranded negative-sense DNA genome. This virus primarily infects cats and dogs.

Affected microorganisms include double-stranded viruses such as Papovaviridae, Adenoviridae, Herpesviridae, Poxviridae, and Hepadnaviridae. With the exception Herpesviridae, these viruses are non-enveloped viruses. Papovaviridae include papillomaviruses causing warts and tumors. Adenoviridae include Mastadenovirus and a variety of viruses capable of infecting the respiratory tract. Herpesviridae include herpes simplex 1 and 2, varicella zoster virus, cytomegalovirus, Epstein-Barr virus, human herpesvirus 6, antibodies to which are now known to be responsible for multiple sclerosis, and human herpesvirus 7. Poxviridae include variola and other pox-producing viruses. Hepadnaviridae include human hepatitis B virus.

Affected microorganisms include bacteria such as *Enterococcus faecium, Staphylococcus aureus, Pseudomonas aeruginosa*, and *Escherichia coli*. Species may be *Staphylococcus, Pseudomonas, Burkholderia, Klebsiella, Clostridium, Bacillus, Enterococcus, Streptococcus, Corynebacterium, Listeria, Neisseria*, and Enterobacteriaceae (which includes the genera *Escherichia, Salmonella*, and *Shigella*). The coliforms are Gram-negative rods, generally in the family Enterobacteriaceae. Some coliforms colonize the intestinal tract of humans and other animals. Some coliforms are associated with disease. Surfaces and liquids can also be contaminated with these bacteria.

Affected microorganisms include fungi such as *Candida albicans*, which causes yeast infection of the oral cavity known as thrush and an infection of the female reproductive tract known as vulvovaginitis.

Each of the light-activated antimicrobial devices disclosed herein includes a light source and a light-activated antimicrobial article. The light-activated antimicrobial article includes a photosensitizer and a viscoelastic material adapted to receive light from the light source. Light from the light source enters the viscoelastic material and is managed so that it can reach the photosensitizer. In some embodiments, the viscoelastic material being adapted to transport light by total internal reflection, is disposed between two substrates, each substrate having a refractive index less than that of the viscoelastic material, such that it can function as a cladding layer. The light-activated antimicrobial device kills or inhibits the growth of an affected microorganism. Presumably, light-activated antimicrobial activity is observed because the photosensitizer absorbs light from the light source and transfers energy from the light to form a reactive species which then kills or inhibits the growth of a affected microorganism. The reactive species may comprise singlet oxygen and other reactive species such as hydrogen peroxide, hydroxyl radical, superoxide radical anion, photosensitizer radical and many other radicals that may be formed depending upon the particular environment of the photosensitizer.

Figure 1B:
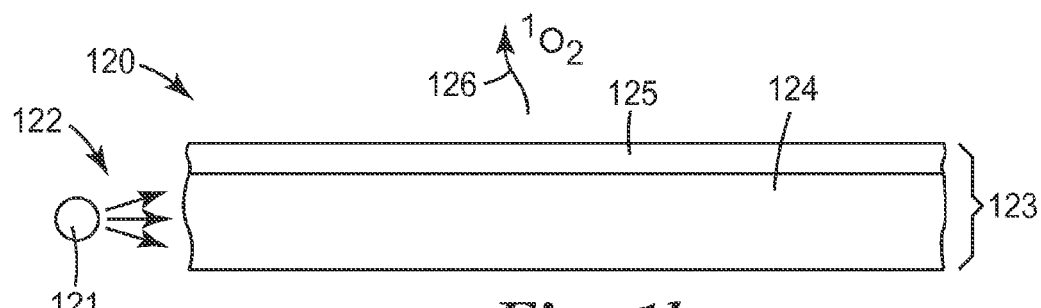

FIG. 1a shows a schematic cross section of exemplary light-activated antimicrobial device 100 comprising light source 101 and light-activated antimicrobial article 103. Article 103 comprises photosensitizer and viscoelastic material. Light source 101 emits light represented by rays 102 that enter the viscoelastic material via input surface 104. Light within the viscoelastic material is absorbed by the photosensitizer such that the photosensitizer generates one or more reactive species that can exit the material. The reactive species is shown as singlet oxygen, $^1O_2$, and exits the viscoelastic material as indicated by ray 105. FIG. 1b shows a schematic cross section of another possible configuration of the light-activated antimicrobial device. Light-activated antimicrobial device 120 comprises light source 121 and light-activated antimicrobial article 123. Article 123 comprises photosensitive layer 125 disposed on viscoelastic material 124. The photosensitizer layer comprises the photosensitizer. At least a portion of the light delivered by the viscoelastic material is absorbed by the photosensitizer such that the photosensitizer generates one or more reactive species that can exit the photosensitive layer. The reactive species is shown as singlet oxygen and exits the photosensitive layer as indicated by ray 126.

The viscoelastic material manages at least some of the light emitted by the light source. The viscoelastic material manages the light in that it distributes and/or delivers the light to one or more desired locations, areas, etc. of the material, so that at least a portion of the light can be absorbed by the photosensitizer. These desired locations, areas, etc. may be different for each device, depending on the overall design of the device, the desired efficiency of the device, etc. For example, if the photosensitizer is incorporated as a gradient within the viscoelastic material, then the material may distribute and deliver light such that a reactive species is generated uniformly or nearly uniformly. For another example, if the photosensitizer is disposed as a photosensitive layer at specific locations on a surface of the viscoelastic material, or at an interface of the material with some substrate, then the material may deliver light to those specific locations.

The viscoelastic material may manage light such that a certain amount of light that enters the viscoelastic layer is absorbed by the photosensitizer. In general, the photosensitizer may absorb light of a particular wavelength or range of wavelengths, for example, if the photosensitizer is a dye. The light emitted by the light source may be white light. The light emitted by the light source may have a particular wavelength or range of wavelengths and this light may be selected depending on the absorption characteristics of the photosensitizer. Given an amount of light that enters the viscoelastic material and that can be absorbed by the photosensitizer, the viscoelastic material may manage light such that greater than about 10%, greater than about 50%, or greater than about 80% of this light is absorbed by the photosensitizer. Given an amount of light that enters the viscoelastic material and that can be absorbed by the photosensitizer, the viscoelastic material may manage light such that from about 10 to about 99%, or from about 30 to about 70% of this light is absorbed by the photosensitizer. Absorbance can be measured using absorption spectroscopy and by applying the Beer-Lambert law.

In general, the viscoelastic material manages light according to the principles of geometric optics, specifically the law of refraction and the principle of total internal reflection. These principles can be applied in conjunction with ray tracing techniques to determine theoretically how light can propagate, reflect and/or refract within the material. This behavior of light may vary according to any number of variables such as the surface structure of the viscoelastic material, the structure of an interface between the material and a substrate in contact with the material, the material compositions of the material and the substrate, and the angular distribution of light that enters the material. These optical principles are well known and are not presented here; for a detailed description of the behavior of light, see for example: D. S. Falk et al. in "Seeing the Light", John Wiley and Sons, Inc., 1986, pp. 53-56, and the Sherman et al. references cited above.

In general, total internal reflection occurs when light having a particular angular component or distribution is incident upon an interface at one or more angles greater than the critical angle $\theta_c$. An optically smooth surface, as used herein, means that the surface is smooth enough such that light incident upon the surface is not affected undesirably by the surface, e.g., the surface is free of defects having at least one dimension larger than the wavelength of the incident light. The optically smooth surface allows at least some of the light entering the viscoelastic material to be reflected at the surface such that this light continues to propagate within the layer according to the principle of total internal reflection. For reflection of light incident on an optically smooth surface, the observed reflection angle is within about 10° of the calculated reflection angle. Total internal reflection occurs if a predetermined amount, or at least within about 10% of a predetermined amount, of light does not escape the viscoelastic material unless it is intentionally extracted from the material.

In general, light propagating within the viscoelastic material is either reflected or extracted from the material. For reflection of light incident on an optically smooth surface, the observed reflection angle is within about 10° of the calculated reflection angle. Likewise, for refraction of light incident on an optically smooth surface, the observed transmittance angle is within about 10° of the calculated transmittance angle. Total internal reflection occurs if a predetermined amount, or at least within about 10% of a predetermined amount, of light does not escape the viscoelastic material unless it is intentionally extracted from the material.

The light source is positioned relative to the viscoelastic material such that at least some of the light emitted by the light source enters the material and, in some embodiments, is transported within the material by total internal reflection.

Figure 2:
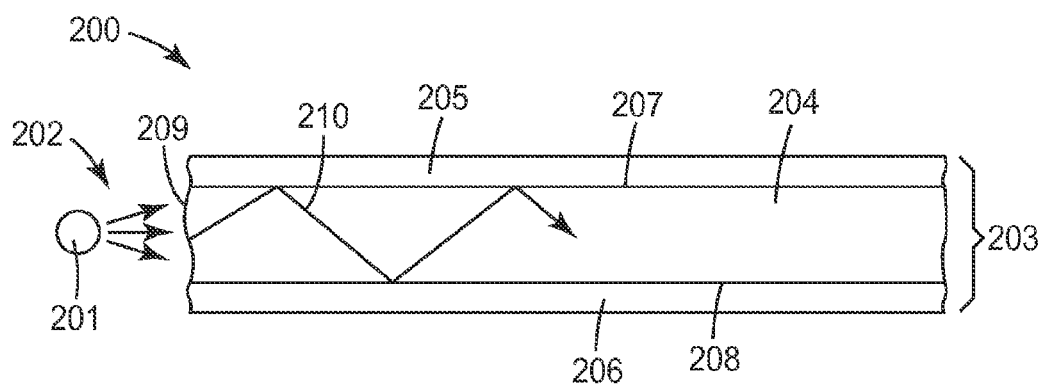

FIG. 2 shows a schematic cross section of exemplary light-activated antimicrobial device 200 comprising light source 201 and light-activated antimicrobial arcticle 203. Article 203 comprises viscoelastic material 204 disposed between substrates 205 and 206. The photosensitizer is incorporated into the viscoelastic material such that the photosensitizer and viscoelastic material form a single body, layer, etc. Light source 201 emits light represented by rays 202 that enter viscoelastic material 204 via input surface 209. Light represented by single ray 210 is transported within the viscoelastic material by total internal reflection. At least a portion of the viscoelastic material has an optically smooth surface 207 and/or 208. One of the substrates may comprise skin of a patient.

In some embodiments, one of the substrates has a refractive index less than that of the viscoelastic material so that skin of a patient does not extract light. This substrate may comprise an adhesive.

Figure 3:
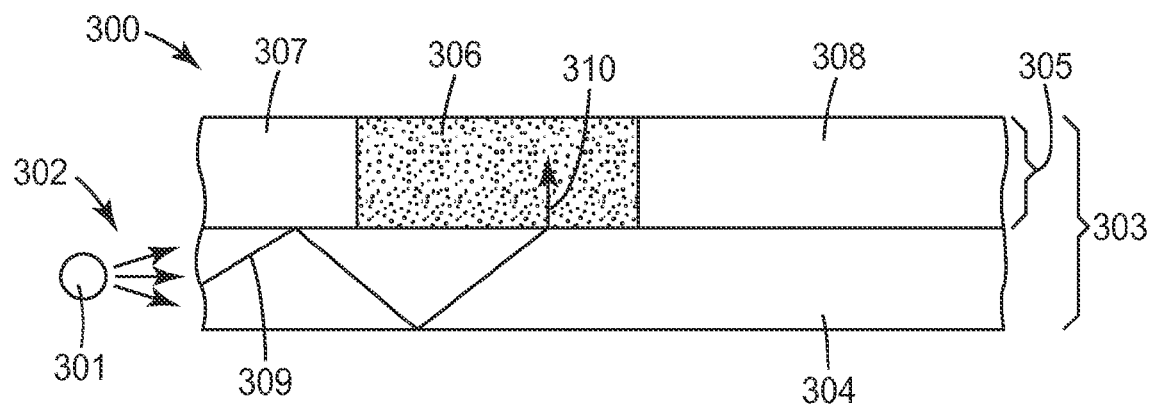

Light transported within the viscoelastic material can be extracted into an adjacent layer such as the photosensitive layer. FIG. 3 shows a schematic cross section of exemplary light-activated antimicrobial device 300 comprising light source 301 and light-activated antimicrobial article 303. Article 303 comprises viscoelastic material 304 and photosensitive layer 305 is disposed on the material. The photosensitive layer comprises regions of two or more different materials 306, 307 and 308. Light represented by rays 302 is emitted from light source 301 and at least some of this light enters viscoelastic material 304 as represented by single ray 309. When the transported light strikes the interface with region 307, the light is reflected and continues to propagate within the material. When the transported light strikes the interface with region 310, the light is extracted into the region, i.e., into photosensitive layer 305. In this particular embodiment, region 306 may comprise the photosensitizer and regions 307 and 308 may comprise a polymeric material.

The photosensitive layer may extract greater than about 10%, greater than about 50%, or greater than about 80% of light transported within the viscoelastic material. The photosensitive layer may extract from about 10 to about 99%, or from about 30 to about 70%, of light transported within the viscoelastic material. As described above, given an amount of light that enters the viscoelastic material and that can be absorbed by the photosensitizer, the photosensitizer may absorb greater than about 10%, greater than about 50%, or greater than about 80% of this light. As described above, given an amount of light that enters the viscoelastic material and that can be absorbed by the photosensitizer, the photosensitizer may absorb from about 10 to about 99%, or from about 30 to about 70% of this light.

The viscoelastic material may manage light such that a certain amount of light that enters the viscoelastic layer is absorbed by the photosensitizer. In general, the photosensitizer may absorb light of a particular wavelength or range of wavelengths, for example, if the photosensitizer is a dye. The light emitted by the light source may be white light. The light emitted by the light source may have a particular wavelength or range of wavelengths and this light may be selected depending on the absorption characteristics of the photosensitizer. Given an amount of light that enters the viscoelastic material and that can be absorbed by the photosensitizer, the viscoelastic material may manage light such that greater than about 10%, greater than about 50%, or greater than about 80% of this light is absorbed by the photosensitizer.

The viscoelastic material may comprise one or more viscoelastic materials. In general, viscoelastic materials exhibit both elastic and viscous behavior when undergoing deformation. Elastic characteristics refer to the ability of a material to return to its original shape after a transient load is removed. One measure of elasticity for a material is referred to as the tensile set value which is a function of the elongation remaining after the material has been stretched and subsequently allowed to recover (destretch) under the same conditions by which it was stretched. If a material has a tensile set value of 0%, then it has returned to its original length upon relaxation, whereas if the tensile set value is 100%, then the material is twice its original length upon relaxation. Tensile set values may be measured using ASTM D412. Useful viscoelastic materials may have tensile set values of greater than about 10%, greater than about 30%, or greater than about 50%; or from about 5 to about 70%, from about 10 to about 70%, from about 30 to about 70%, or from about 10 to about 60%.

Viscous materials that are Newtonian liquids have viscous characteristics that obey Newton's law which states that stress increases linearly with shear gradient. A liquid does not recover its shape as the shear gradient is removed. Viscous characteristics of useful viscoelastic materials include flowability of the material under reasonable temperatures such that the material does not decompose.

The viscoelastic material may have properties that facilitate sufficient contact or wetting with at least a portion of a material designed to extract light from the material, e.g., the retroreflective film or substrate, such that the viscoelastic material and the retroreflective film are optically coupled. Light can then be extracted from the viscoelastic material. The viscoelastic material is generally soft, compliant and flexible. Thus, the viscoelastic material may have an elastic modulus (or storage modulus G') such that sufficient contact can be obtained, and a viscous modulus (or loss modulus G") such that the layer doesn't flow undesirably, and a damping coefficient (G"/G', tan D) for the relative degree of damping of the layer.

Useful viscoelastic materials may have a storage modulus, G', of less than about 300,000 Pa, measured at 10 rad/sec and a temperature of from about 20 to about 22° C. Useful viscoelastic materials may have a storage modulus, G', of from about 30 to about 300,000 Pa, measured at 10 rad/sec and a temperature of from about 20 to about 22° C. Useful viscoelastic materials may have a storage modulus, G', of from about 30 to about 150,000 Pa, measured at 10 rad/sec and a temperature of from about 20 to about 22° C. Useful viscoelastic materials may have a storage modulus, G', of from about 30 to about 30,000 Pa, measured at 10 rad/sec and a temperature of from about 20 to about 22° C. Useful viscoelastic materials may have a storage modulus, G', of from about 30 to about 150,000 Pa, measured at 10 rad/sec and a temperature of from about 20 to about 22° C., and a loss tangent (tan d) of from about 0.4 to about 3. Viscoelastic properties of materials can be measured using Dynamic Mechanical Analysis according to, for example, ASTM D4065, D4440, and D5279.

In some embodiments, the viscoelastic material comprises a pressure sensitive adhesive (PSA) as described in the Dalquist criterion line (as described in Handbook of Pressure Sensitive Adhesive Technology, Second Ed., D. Satas, ed., Van Nostrand Reinhold, New York, 1989.)

The viscoelastic material may have a particular peel force or at least exhibit a peel force within a particular range. For example, the viscoelastic material may have a 90° peel force of from about 50 to about 3000 On, from about 300 to about 3000 On, or from about 500 to about 3000 Win. Peel force may be measured using a peel tester from IMASS.

In some embodiments, the viscoelastic material comprises an optically clear material having high light transmittance of from about 80 to about 100%, from about 90 to about 100%, from about 95 to about 100%, or from about 98 to about 100% over at least a portion of the spectrum of from about 200 to about 900 nm, or from about 400 to 750 nm. In some embodiments, the viscoelastic material has a haze value of less than about 5%, less than about 3%, or less than about 1%. In some embodiments, the viscoelastic material has a haze value of from about 0.01 to less than about 5%, from about 0.01 to less than about 3%, or from about 0.01 to less than about 1%. Percent transmission may be determined according to Beer's Law using absorption spectroscopy. Haze values in transmission can be determined using a haze meter according to ASTM D1003.

In some embodiments, the viscoelastic material comprises an optically clear material having high light transmittance and a low haze value. High light transmittance may be from about 90 to about 100%, from about 95 to about 100%, or from about 99 to about 100% over at least a portion of the visible light spectrum (about 400 to about 700 nm), and haze values may be from about 0.01 to less than about 5%, from about 0.01 to less than about 3%, or from about 0.01 to less than about 1%. The viscoelastic material may also have a light transmittance of from about 50 to about 100%. In this context, the portion of the visible light spectrum may be at least one of the peak absorption wavelengths of at least one of the photosensitizers if more than one is used.

In some embodiments, the viscoelastic material is hazy and diffuses light, particularly visible light. A hazy viscoelastic material may have a haze value of greater than about 5%, greater than about 20%, or greater than about 50%. A hazy viscoelastic material may have a haze value of from about 5 to about 90%, from about 5 to about 50%, or from about 20 to about 50%.

The viscoelastic material may have a refractive index in the range of from about 1.3 to about 2.6, 1.4 to about 1.7, or from about 1.5 to about 1.7. The particular refractive index or range of refractive indices selected for the viscoelastic material may depend on the overall design of the light-activated antimicrobial device and the particular application for which the device is intended.

The viscoelastic material generally comprises at least one polymer. The viscoelastic material may comprise at least one PSA. PSAs are useful for adhering together adherends and exhibit properties such as: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process. A quantitative description of PSAs can be found in the Dalquist reference cited above.

Useful PSAs are described in detailed in the Sherman et al. References cited above. Only a brief description of useful PSAs is included here. Exemplary poly(meth)acrylate PSAs are derived from: monomer A comprising at least one mono ethylenically unsaturated alkyl(meth)acrylate monomer and which contributes to the flexibility and tack of the PSA; and monomer B comprising at least one mono ethylenically unsaturated free-radically copolymerizable reinforcing monomer which raises the TG of the PSA and contributes to the cohesive strength of the PSA. Monomer B has a homopolymer glass transition temperature (TG) higher than that of monomer A. As used herein, (meth)acrylic refers to both acrylic and methacrylic species and likewise for (meth) acrylate.

Preferably, monomer A has a homopolymer TG of no greater than about 0° C. Preferably, the alkyl group of the (meth)acrylate has an average of about 4 to about 20 carbon atoms. Examples of monomer A include 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isobornyl acrylate. The alkyl group can comprise ethers, alkoxy ethers, ethoxylated or propoxylated methoxy(meth)acrylates. Monomer A may comprise benzyl acrylate. Monomer A may comprise a urethane acrylate.

Preferably, monomer B has a homopolymer TG of at least about 10° C., for example, from about 10 to about 50° C. Monomer B may comprise (meth)acrylic acid, (meth)acrylamide and N-monoalkyl or N-dialkyl derivatives thereof, or a (meth)acrylate. Examples of monomer B include N-hydroxyethyl acrylamide, diacetone acrylamide, N,N-dimethyl acrylamide, N, N-diethyl acrylamide, N-ethyl-N-aminoethyl acrylamide, N-ethyl-N-hydroxyethyl acrylamide, N,N-dihydroxyethyl acrylamide, t-butyl acrylamide, N,N-dimethylaminoethyl acrylamide, and N-octyl acrylamide. Other examples of monomer B include itaconic acid, crotonic acid, maleic acid, fumaric acid, 2,2-(diethoxy)ethyl acrylate, 2-hydroxyethyl acrylate or methacrylate, 3-hydroxypropyl acrylate or methacrylate, methyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl formamide, N-vinyl acetamide, N-vinyl pyrrolidone, and N-vinyl caprolactam. Monomer B may comprise an epoxy acrylate.

In some embodiments, the (meth)acrylate PSA is formulated to have a resultant TG of less than about 0° C. and more preferably, less than about −10° C. Such (meth)acrylate PSAs include about 60 to about 98% by weight of at least one monomer A and about 2 to about 40% by weight of at least one monomer B, both relative to the total weight of the (meth)acrylate PSA copolymer.

Useful PSAs include natural rubber-based and synthetic rubber-based PSAs. Rubber-based PSAs include butyl rubber, copolymers of isobutylene and isoprene, polyisobutylene, homopolymers of isoprene, polybutadiene, and styrene/butadiene rubber. These PSAs may be inherently tacky or they may require tackifiers. Tackifiers include rosins and hydrocarbon resins.

Useful PSAs include thermoplastic elastomers. These PSAs include styrene block copolymers with rubbery blocks of polyisoprene, polybutadiene, poly(ethylene/butylene), poly(ethylene-propylene). Resins that associate with the rubber phase may be used with thermoplastic elastomer PSAs if the elastomer itself is not tacky enough. Examples of rubber phase associating resins include aliphatic olefin-derived resins, hydrogenated hydrocarbons, and terpene phenolic resins. Resins that associate with the thermoplastic phase may be used with thermoplastic elastomer PSAs if the elastomer is not stiff enough. Thermoplastic phase associating resins include polyaromatics, coumarone-indene resins, resins derived from coal tar or petroleum.

Useful PSAs include tackified thermoplastic-epoxy pressure sensitive adhesives as described in U.S. Pat. No.

7,005,394 (Ylitalo et al.). These PSAs include thermoplastic polymer, tackifier and an epoxy component.

Useful PSAs include polyurethane pressure sensitive adhesive as described in U.S. Pat. No. 3,718,712 (Tushaus). These PSAs include crosslinked polyurethane and a tackifier.

Useful PSAs include polyurethane acrylate as described in US 2006/0216523 (Shusuke). These PSAs include urethane acrylate oligomer, plasticizer and an initiator.

Useful PSAs include silicone PSAs such as polydiorganosiloxanes, polydiorganosiloxane polyoxamides and silicone urea block copolymers described in U.S. Pat. No. 5,214,119 (Leir, et al). The silicone PSAs may be formed from a hyrosilylation reaction between one or more components having silicon-bonded hydrogen and aliphatic unsaturation. The silicone PSAs may include a polymer or gum and an optional tackifying resin. The tackifying resin may comprise a three-dimensional silicate structure that is endcapped with trialkylsiloxy groups.

Useful silicone PSAs may also comprise a polydiorganosiloxane polyoxamide and an optional tackifier as described in U.S. Pat. No. 7,361,474 (Sherman et al.) incorporated herein by reference. Useful tackifiers include silicone tackifying resins as described in U.S. Pat. No. 7,090,922 B2 (Zhou et al.) incorporated herein by reference.

The PSA may be crosslinked to build molecular weight and strength of the PSA. Crosslinking agents may be used to form chemical crosslinks, physical crosslinks or a combination thereof, and they may be activated by heat, UV radiation and the like.

In some embodiments, the viscoelastic material comprises a PSA formed from a (meth)acrylate block copolymer as described in U.S. Pat. No. 7,255,920 B2 (Everaerts et al.). In general, these (meth)acrylate block copolymers comprise: at least two A block polymeric units that are the reaction product of a first monomer composition comprising an alkyl methacrylate, an aralkyl methacrylate, an aryl methacrylate, or a combination thereof, each A block having a TG of at least 50° C., the methacrylate block copolymer comprising from 20 to 50 weight percent A block; and at least one B block polymeric unit that is the reaction product of a second monomer composition comprising an alkyl(meth)acrylate, a heteroalkyl(meth)acrylate, a vinyl ester, or a combination thereof, the B block having a TG no greater than 20° C., the (meth)acrylate block copolymer comprising from 50 to 80 weight percent B block; wherein the A block polymeric units are present as nanodomains having an average size less than about 150 nm in a matrix of the B block polymeric units.

In some embodiments, the viscoelastic material comprises a clear acrylic PSA, for example, those available as transfer tapes such as VHB™ Acrylic Tape 4910F from 3M Company and 3M™ Optically Clear Laminating Adhesives (8140 and 8180 series).

In some embodiments, the viscoelastic material comprises a PSA formed from at least one monomer containing a substituted or an unsubstituted aromatic moiety as described in U.S. Pat. No. 6,663,978 B1 (Olson et al.).

In some embodiments, the viscoelastic material comprises a copolymer as described in U.S. Ser. No. 11/875,194 (Determan et al.), comprising (a) monomer units having pendant bephenyl groups and (b) alkyl(meth)acrylate monomer units.

In some embodiments, the viscoelastic material comprises a copolymer as described in U.S. Provisional Application Ser. No. 60/983,735 (Determan et al.), comprising (a) monomer units having pendant carbazole groups and (b) alkyl (meth)acrylate monomer units.

In some embodiments, the viscoelastic material comprises an adhesive as described in U.S. Provisional Application Ser. No. 60/986,298 (Schaffer et al.), comprising a block copolymer dispersed in an adhesive matrix to form a Lewis acid-base pair. The block copolymer comprises an AB block copolymer, and the A block phase separates to form microdomains within the B block/adhesive matrix. For example, the adhesive matrix may comprise a copolymer of an alkyl(meth)acrylate and a (meth)acrylate having pendant acid functionality, and the block copolymer may comprise a styrene-acrylate copolymer. The microdomains may be large enough to forward scatter incident light, but not so large that they backscatter incident light. Typically these microdomains are larger than the wavelength of visible light (about 400 to about 700 nm). In some embodiments the microdomain size is from about 1.0 to about 10 um.

The viscoelastic material may comprise a stretch releasable PSA. Stretch releasable PSAs are PSAs that can be removed from a substrate if they are stretched at or nearly at a zero degree angle. In some embodiments, the viscoelastic material or a stretch release PSA used in the viscoelastic material has a shear storage modulus of less than about 10 MPa when measured at 1 rad/sec and −17° C., or from about 0.03 to about 10 MPa when measured at 1 rad/sec and −17° C. Stretch releasable PSAs may be used if disassembling, reworking, or recycling is desired.

In some embodiments, the stretch releasable PSA may comprise a silicone-based PSA as described in U.S. Pat. No. 6,569,521 B1 (Sheridan et al.) or U.S. Provisional Application No. 61/020,423 (Sherman et al.) and 61/036,501 (Determan et al.). Such silicone-based PSAs include compositions of an MQ tackifying resin and a silicone polymer. For example, the stretch releasable PSA may comprise an MQ tackifying resin and an elastomeric silicone polymer selected from the group consisting of urea-based silicone copolymers, oxamide-based silicone copolymers, amide-based silicone copolymers, urethane-based silicone copolymers, and mixtures thereof.

In some embodiments, the stretch releasable PSA may comprise an acrylate-based PSA as described in U.S. Provisional Application No. 61/141,767 (Yamanaka et al.) and 61/141,827 (Tran et al.) Such acrylate-based PSAs include compositions of an acrylate, an inorganic particle and a crosslinker. These PSAs can be a single or multilayer.

The viscoelastic material include additional antimicrobial agents such as silver-based compounds or "sparingly soluble" silver compounds, as described in US 2006/0035039 A1 (Ylitalo, et al.), including silver oxide, silver sulfate, silver acetate, silver chloride, silver phosphate, silver stearate, silver thiocyanate, silver proteinate, silver carbonate, silver sulfadiazine, silver alginate, and combinations thereof. Sparingly soluble silver compounds may be defined as those which are soluble in water, without the assistance of a solubilizer, up to about 10 grams per liter. Other additional antimicrobial agents include biguanide compounds such as chlorhexidine derivatives, alcohols such as ethanol or isopropanol, aldehydes such as glutaraldehyde, phenolics such as phenol, triclosan and chloroxylenol, iodine and iodophors such as povidone iodine, quaternary ammonium compounds such as benzalkonium chloride and cetylpyridinium chloride, and oxidizing agents such as hypochlorites, chloramines and chlorates.

The viscoelastic material may include particles such as nanoparticles (diameter from about 0.005 to about 1 um), microspheres (diameter of 1 to about 10 um), or fibers.

The viscoelastic material may be in the form of a layer, sheet, film, etc. which may be cut into various shapes as described below. The thickness of the viscoelastic material is not particularly limited as long as the material can function as desired. The thickness of the viscoelastic material may be selected based on or in conjunction with the light source. For example, design parameters may limit or even require that a particular light source(s) be used, and there may be a minimum amount, or range of amounts, of light that is required to enter the viscoelastic material. Thus, the thickness of the viscoelastic material may be selected so that the required amount of light from a given light source can enter the material. A maximum thickness of the viscoelastic material may be required for use in devices designed to be particularly thin. Exemplary thicknesses for the viscoelastic material range from about 0.4 mil to about 1000 mil, from about 1 mil to about 300 mil, from about 1 mil to about 60 mil, or from about 0.5 mil to about 30 mil.

The photosensitizer may comprise any material that can transfer energy of light extracted from the viscoelastic material such that antimicrobial activity occurs. Antimicrobial activity may result from the generation of one or more reactive species such as singlet oxygen, hydrogen peroxide, hydroxyl radical, superoxide radical anion, photosensitizer radical and many other radicals that may be formed depending upon the particular environment of the photosensitizer.

In general, the photosensitizer comprises a material that absorbs in the invisible or visible light spectrum. The photosensitizer may absorb at a particular wavelength or over a range of wavelengths, anywhere from about 200 to about 750 nm or from about 400 to about 750 nm. Suitable photosensitizers include dyes which may absorb light within a fairly narrow range within about 400 to about 750 nm. Suitable dyes include any one or more of the following classes: porphyrins, fluoresceines, phenothiaziniums, phthalocyanines, acridines, xanthenes, thionines, oxazines, triphenylmethanes, C.I. azure dyes, anthracenes, anthraquinones, and quinacrines. The photosensitizer may comprise Acridine Yellow G, Rose Bengal, Erythrosin, Phloxin B, Methylene Blue, Toluidine Blue, Tetratolylphorphine, Tetraphenylporphine, and/or Acridine Orange. The photosensitizer may comprise a platinum- or palladium-containing compound wherein the platinum or palladium is complexed to a nitrogen atom of a heterocycle; these compounds are described in U.S. Pat. No. 6,248,733 B1 (Landgrebe et al.)

For yet another example, the photosensitizer may comprise anatase titanium dioxide as described, for example, in WO 99/62822 (Kobayashi et al.) and CA 1038135 (Lange et al.).

For yet another example, the photosensitizer may comprise a composition that releases a gas such as chlorine dioxide, sulfur dioxide, hydrogen sulfide, chlorine, dichlorine monoxide, hydrocyanic acid, nitrogen dioxide, nitric oxide and nitrous oxide. These exemplary compositions are described in U.S. Pat. No. 7,273,567 B1 (Wellinghoff et al.). In general, the compositions that release a gas comprise a catalyst that is activated by electromagnetic radiation (absorbs typically UV and/or visible), and a solid containing anions capable of being oxidized or reacted to generate the gas. Exemplary catalysts are selected from the group consisting of metal oxides, metal sulfides, metal chalcogenites, metal phosphides, metal arsenides, non-metallic semiconductors, polymeric semiconductors, photoactive homopolyanions and photoactive heteropolyions. Exemplary anions are selected from the group consisting of chlorite, bisulfite, sulfite, hydrosulfide, sulfide, hypochlorite, cyanide and nitrate. In one example, the catalyst comprises anatase titanium dioxide particles having a coating of sodium chloride.

The photosensitizer may be covalently bound to a larger molecule, macromolecule or polymer. For example, the photosensitizer may comprise a polymer having pendant photosensitizer groups. A polymer having a pendant photosensitizer group may be made by addition and/or condensation polymerization of one or more monomers having pendant photosensitizer groups with other monomers, grafting one or more photosensitizer groups onto a mainchain or subchain of a polymer that is previously formed, or by crosslinking. The polymer having a covalently bound photosensitizer may be a polyacrylate, polymethacrylate, polyurethane, polyolefin, polyethylene imine, polycarbonate, cellulose, polyester, polyimide, polyurea, polyamide, polyether or a combination thereof. The polymer having a covalently bound photosensitizer may comprise a polyurethane or polyolefin having platinum- or palladium-containing groups wherein the platinum or palladium is complexed to a nitrogen atom of a heterocycle; these polymers are described in U.S. Pat. No. 6,432,396 B1 (Landgrebe et al.). The polymer having a covalently bound photosensitizer may comprise polystyrene/divinylbenzene copolymer having pendant rose bengal groups.

Monomers having pendant photosensitizing groups may be made by functionalizing the nitrogen atom of 4-vinylpyridine.

Photosensitizers which may be used in grafting include those having reactive pendant groups such as carboxylic acid, hydroxyl, amino, thiol or alkene functionality.

The photosensitizer may be free or not free depending on the particular environment of the photosensitizer. For example, the photosensitizer may be ionically bonded to a larger molecule, macromolecule, polymer or particle. Ionic bonding is typically an electrostatic interaction between oppositely charged species. For example, the photosensitizer may be anionically or cationically charged and ionically bonded to a larger molecule, macromolecule, polymer or particle having the opposite charge. If, for example, the photosensitizer is ionically bonded to a polymer and the combination of the two is somewhat hydrophilic, then exposure to enough moisture may cause the photosensitizer to mobilize during storage or use of the article, device or method. However, if the combination of the two is hydrophobic, then the photosensitizer may remain immobilized during storage or use of the article, device or method.

The photosensitizer may be disposed relative to the viscoelastic material in any manner, as long as light emitted from the light source can be absorbed by the photosensitizer. For example, the photosensitizer may be incorporated into the viscoelastic material such that the two form a single layer or other form. The photosensitizer may be incorporated in a free or bound form as described above. The photosensitizer may be incorporated uniformly or nearly uniformly throughout the viscoelastic material. The photosensitizer may be incorporated as a gradient throughout the viscoelastic material. The photosensitizer may be incorporated in discrete areas such as zones, stripes etc. throughout the viscoelastic material.

A photosensitive layer comprising the photosensitizer may be disposed on the viscoelastic material. In some embodiments, the photosensitive layer consists essentially of the photosensitizer. For example, a solution of the photosensitizer may be coated on the viscoelastic material and the resulting wet layer dried to provide a dry coating of the photosensitizer. Photosensitizer may be deposited as a continuous layer either completely or partially covering the viscoelastic material. Photosensitizer may also be deposited uniformly or in some type of pattern or other discontinuous layout on the viscoelastic material. Photosensitizer may also be disposed on the substrate onto which the device will be attached uniformly or patterned.

The photosensitive layer may comprise the photosensitizer and a porous or nonporous material.

In some embodiments, the photosensitive layer comprises the photosensitizer and a fibrous material. Suitable fibrous materials comprise natural and/or synthetic materials such as silk, nylon, cotton, aramid and polyolefins and copolymers thereof. The fibrous material may comprise a woven material such as a cloth formed by weaving. The fibrous material may comprise a nonwoven material wherein long fibers are bonded together by chemical, mechanical, heat or solvent treatment. For example, fabric may be wet with a solution of the photosensitizer and the resulting wet fabric dried to provide a dry fabric comprising the photosensitizer deposited on fibres that make up the fabric.

In some embodiments, the photosensitive layer comprises the photosensitizer and a membrane which serves as a selective barrier between two components of a composition, some of which are allowed to pass through the membrane and some which are not. The membrane may be inorganic, polymeric or a biological membrane. The membrane may be made by a process known as thermally induced phase separation (TIPS) which uses a polymer or polymer blend, a nucleating agent and a diluent. Membranes made using TIPS can be customized to have an average pore size of anywhere from about 0.05 to about 20 um. The use of TIPS to make membranes is described in WO 2009/048743 A1 (Mrozinski); US 2005/0058821 A1 (Smith et al.); US 2006/148915 A1 (Floyd et al.); and US2003/228459 A1 (Mrozinski et al.).

In some embodiments, the photosensitive layer comprises the photosensitizer and a polymeric material. For example, the photosensitizer may be incorporated into a polymeric material such that the two form a single layer. The photosensitizer may be incorporated in a free or bound form as described above. A polymeric material having an incorporated photosensitizer may be used to make fibrous articles described above.

Any polymeric material may be used as long as the light-activated antimicrobial device can function as desired. The photosensitizer may need to be compatible with the polymeric material, e.g., so that the photosensitizer does not aggregate within the polymeric material which could interfere with absorption of light by the photosensitizer. The polymeric material may need to have little or no absorption of light within a certain range of wavelengths. For example, the polymeric material may need to have little or no absorption within a wavelength range of light intended to be absorbed by the photosensitizer, as this could affect efficiency of the device. It is also important for devices that may be used for extended periods of time that the polymeric material (e.g. binder) not be easily degraded by the oxidizing species produced by the photosensitizer.

The photosensitizer may be used in any amount needed to achieve a desired effect. For example, the photosensitizer may be used in an amount effective in decreasing colony forming units, for example, in an amount of from about 80 to 100%. The photosensitizer may be used in an amount of from about 0.01 to about 10%, or from about 0.1 to about 5%, by weight, and relative to the weight of the layer or material in which the photosensitizer is used.

The light-activated antimicrobial article may further comprise a substrate on which the viscoelastic material is disposed. The substrate may comprise a wide variety of materials depending on the intended properties of the light-activated antimicrobial article. The substrate may be flexible by hand or it may be rigid such that it exhibits little or no flexibility by hand. The substrate may have any bulk three-dimensional shape as is needed for a given application. The substrate may be commensurate in size with the viscoelastic material, or it may be larger or smaller than the viscoelastic material. The substrate may be in the form of a layer, sheet, film, etc. The substrate may comprise a polymeric film, paper, fabric, or a combination thereof. Exemplary thicknesses for the substrate range from about 0.4 mil to about 1000 mil, from about 1 mil to about 300 mil, from about 1 mil to about 60 mil, or from about 0.5 mil to about 30 mil.

The substrate may comprise a reflector that reflects incident light being transported within the viscoelastic material. In this way, for example, light can be transported by total internal reflection and distributed throughout the viscoelastic material, or to specific areas of the material. A substrate reflects incident light if it reflects from about 50 to about 100%, from about 70 to about 100%, from about 90 to about 100% of incident light. The substrate may be selected such that it extracts from about 0 to about 20% of incident light.

The reflector may comprise a specular reflector such that the reflection angle of light is within about 16° of the incident angle. Suitable specular reflectors include mirrors such as a plane mirrors comprising a film of reflecting material coated on a substrate. Suitable reflectors include mirrors that are multilayer optical films. Useful multilayer optical films comprise films having from about 10 to about 10,000 alternating layers of first and second polymer layers wherein the polymer layers comprise polyesters. Exemplary multilayer optical films are described in U.S. Pat. Nos. 5,825,543 and 5,828,488 (Ouderkirk et al.) and additional references cited in any of the Sherman et al. References cited above. Exemplary specular reflectors include those available from 3M™ Company, for example, 3M™ High Intensity Grade Reflective Products such as High Reflective Visible Mirror Film and High Transmission Mirror Film, and Vikuiti™ films such as Vikuiti™ Enhanced Specular Reflector.

The reflector may comprise a diffuse reflector wherein light propagating within the viscoelastic material is reflected and scattered at a surface of the diffuse reflector. For a diffuse reflector, light of a given incident angle reflects with multiple reflection angles wherein at least some of the reflection angles are greater than about 16° of the incident angle. A diffuse reflector may comprise an irregular surface with respect to the wavelength of light being reflected. The diffuse reflector may comprise a layer of organic, inorganic or hybrid organic/inorganic particles disposed on a substrate. The particles may have a diameter of from greater than about 0.01 to about 100 um, from greater than about 0.05 to about 100 um, or from greater than about 0.05 to about 50 um. The particles may be dispersed in a polymeric binder. Binders include one or more polymers and may be, for example, any of the viscoelastic materials described above such as a PSA.

In some embodiments, the substrate comprises a multilayer optical film. Multilayer optical films that are mirrors are described above. Other types of multilayer optical films may also be used, for example, the multilayer optical film may be a reflective film, a polarizer film, a reflective polarizer film, a diffuse blend reflective polarizer film, a diffuser film, a brightness enhancing film, a turning film, a mirror film, or a combination thereof. Exemplary multilayer optical films include 3M™ Vikuiti™ films available from 3M™ Company. Exemplary multilayer optical films are described in the references cited above for multilayer optical films that are mirrors.

The light-activated antimicrobial article may comprise a release liner disposed on the viscoelastic material. Release liners typically have a low adhesion surface for contact with an adhesive layer. Release liners may comprise paper such as Kraft paper, or polymeric films such as poly(vinyl chloride), polyester, polyolefin, cellulose acetate, ethylene vinyl acetate, polyurethane, and the like. The release liner may be coated with a layer of a release agent such as a silicone-containing material or a fluorocarbon-containing material. The release liner may comprise paper or a polymeric film coated with polyethylene which is coated with a silicone-containing material. Exemplary release liners include liners commercially available from CP Films Inc. under the trade designations "T-30" and "T-10" that have a silicone release coating on polyethylene terephthalate film.

In general, the viscoelastic material is adapted to receive at least some light emitted by the light source. In some embodiments, a specially designed input surface may not be needed because the light source can be pressed into the viscoelastic material such that the two are in contact and optical coupling occurs. In some embodiments, the light source may stick to the viscoelastic material, for example, if the material comprises a PSA. In some embodiments, the light source may be embedded in the viscoelastic material.

The light source and the viscoelastic material need not be in contact as described in the following embodiments. In some embodiments, the viscoelastic material comprises an input surface adapted to receive light from the light source. The input surface may have a variety of topographies depending on the optical coupling means and/or the particular light source. The input surface may have an appropriate curvature. The input edge comprising the input surface may have a particular cavity, for example a concave hemispherical cavity, to receive a convex lens of a light source. Alternately, the input surface may have refractive structures such as prisms or lenses to optically couple light from the light source into the viscoelastic material.

The light-activated antimicrobial article may further comprise a substrate on which the viscoelastic material is disposed, and wherein substrate comprises the light source.

In some embodiments, an extractor article disposed between the light source and the input edge may be used to facilitate optical coupling with at least some of the light emitted by the light source. Useful extractor articles may have an appropriate curvature for extracting light from the light source. A coupling material for matching refractive indices of the viscoelastic material and some element of the light source may be used. A crosslinkable material may be used for attaching the viscoelastic material to some part of the light source, and subsequently cured using heat and/or light to form the crosslinked material.

The coupling material may comprise silicone gel. The silicone gel may be crosslinked. The silicone gel may be mixed with a silicone oil. The silicone gel may comprise one or more silicone materials such as, for example, dimethylsilicone, diphenylsilicone, or phenylmethylsilicone. The silicone gel may comprise phenylmethylsilicone moieties that are cross-linked. The silicone gel may comprise phenylmethylsilicone moieties which are cross-linked and phenylmethylsilicone oil. The silicone gel may comprise phenylmethylsilicone moieties which are cross-linked and phenylmethylsilicone oil in a weight ratio from 0.2:1 to 5:1. The silicone gel may comprise crosslinked phenylmethylsilicone. Exemplary use of silicone gels is described in U.S. Pat. No. 7,315,418 (DiZio et al.) incorporated herein by reference.

The light source may be optically coupled to the viscoelastic material such that at least some of the light from the light source can enter the material. For example, a light source may be optically coupled to the viscoelastic material such that greater than 1, greater than 10, greater than 20, greater than 30, greater than 40, greater than 50, greater than 90%, or about 100% of light emitted by the light source enters the viscoelastic material. For another example, a light source may be optically coupled to the viscoelastic material such that from about 1 to about 10%, from about 1 to about 20%, from about 1 to about 30%, from about 1 to about 40%, from about 1 to about 50%, from about 1 to about 100%, from about 1 to about 100%, from about 50 to about 100%, or from about 1 to about 100% of light emitted by the light source enters the viscoelastic material. The light source may emit light having a random or a particular angular distribution.

The light source may comprise any suitable light source. In some embodiments, the light source should emit light near at least one of the peak absorption wavelengths of at least one of the photosensitizers if more than one is used. Exemplary light sources include linear light sources such as cold cathode fluorescent lamps and point light sources such as light emitting diode (LEDs). Exemplary light sources also include organic light-emitting devices (OLEDs), incandescent bulbs, fluorescent bulbs, halogen lamps, UV bulbs, infrared sources, near-infrared sources, lasers, or chemical light sources. In general, the light emitted by the light source may be visible or invisible. At least one light source may be used. For example, from 1 to about 10,000 light sources may be used. The light source may comprise a row of LEDs positioned at or near an edge of the viscoelastic material. The light source may comprise LEDs arranged on a circuit such that light emitted from the LEDs lights up continuously or uniformly the viscoelastic material throughout a desired area. The light source may comprise LEDs that emit light of different colors such that the colors can mix within the viscoelastic material. In this way, a graphic could be designed to appear differently at different times during its use.

The light source may be powered by any suitable means. The light source may be powered using a battery, a DC power supply, an AC to DC power supply, an AC power supply, or a solar photovoltaic cell. The light source may also be powered by motion such as walking. The light source may also be powered remotely, for example by induction, much as an RF identification tag, such that a patient can be free from connecting wires.

Figure 4A:
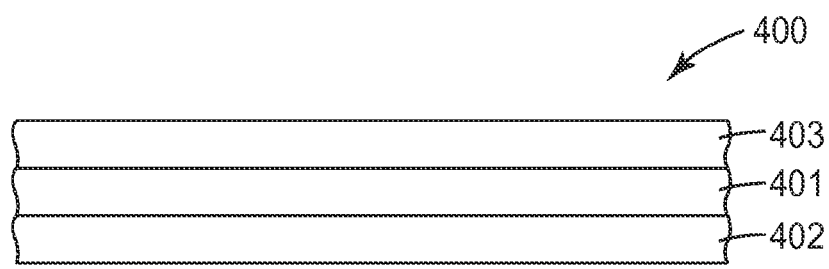
FIGS. 4a and 4b show schematic cross sections of exemplary light-activated antimicrobial articles.

FIG. 4a shows a schematic cross section of an exemplary light-activated antimicrobial article. Light-activated antimicrobial article 400 comprises viscoelastic layer 401 disposed between optional release liner 403 and film backing 402. In one embodiment of article 400, the photosensitizer is incorporated into the viscoelastic material which forms layer 401. The article may be provided with the release liner which can be removed and the viscoelastic layer applied to skin of a patient on the side opposite film backing 402. Useful film backings include elastic film backings which are described below for FIG. 5.

In another embodiment of article 400, the photosensitizer may not be included in viscoelastic layer 401. Instead, the photosensitizer may be formulated in a lotion, foam, mousse, splash, aerosol or other topical composition which is provided separately from the light-activated antimicrobial article or device. The topical composition may be any composition in which the photosensitizer can be formulated homogeneously and allows the photosensitizer to function as desired. Lotions are typically characterized as topical compositions and include creams and gels. Many lotions are oil-in-water emulsions but water-in-oil preparations are also known. Useful lotions include those that are antibacterial or known as hand cream or face cream. An exemplary lotion composition is 3M™ Avagard™ D instant hand antiseptic which comprises ethyl alcohol in a moisturizing base.

In some embodiments, the topical composition comprises the photosensitizer, and the composition has a refractive index less than that of the viscoelastic material such that light can be kept in total internal reflection against the skin. Particles could be included wherein the particles act to extract light into the topical composition thus exposing the photosensitizer.

The amount of particles used in the topical composition can be adjusted so that the composition is homogenous and can be spread uniformly. The topical composition could be applied thicker or thinner relative to other areas in which the composition is applied. For example, the topical composition could be applied thicker over areas to be treated and thinner over areas that do not need to be treated.

In yet another embodiment of article 400, the photosensitizer may be included in viscoelastic layer 401 and provided separately in a lotion.

Figure 4B:
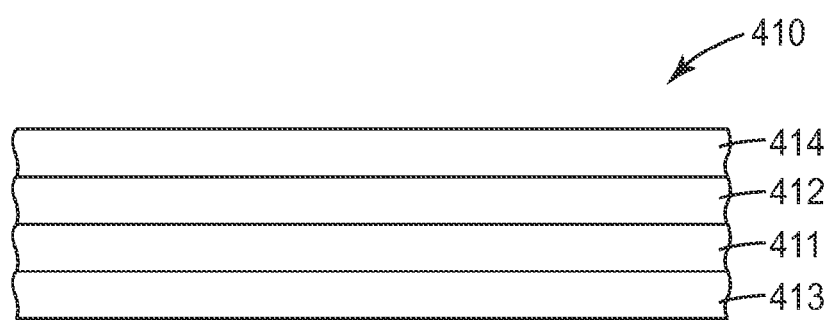

FIG. 4b shows a schematic cross section of an exemplary light-activated antimicrobial article. Light-activated antimicrobial article 410 comprises viscoelastic layer 411 disposed between photosensitive layer 412 and film backing 413. Liner 414 is disposed on photosensitive layer 412 opposite the viscoelastic layer. Liner 414 can be removed and the photosensitive layer applied to skin of a patient on the side opposite viscoelastic layer 411.

The light-activated antimicrobial articles and devices may be incorporated into a therapeutic device. For example, the light-activated antimicrobial articles and devices disclosed herein may be used in conformal patches for providing light therapy to tissue. Exemplary conformal patches are described in U.S. Pat. No. 6,096,066 (Chen et al.), incorporated herein by reference. Additional therapeutic devices are described in U.S. 2005/0070976 A1 (Samuel et al.); Electronics World, October 2007; and LEDs Magazine, November 2006; all of which are incorporated herein by reference.

Figure 5:
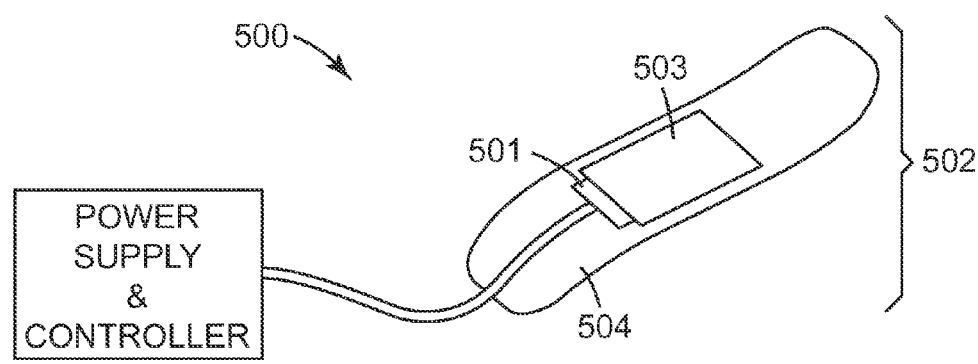
FIGS. 5 and 6 show perspective views of exemplary light-activated antimicrobial devices.

FIG. 5 shows a perspective view of exemplary light-activated antimicrobial device 500 which may be used as a wound dressing for light therapy. In this embodiment, device 500 comprises light source 501 electrically connected to a power supply with microcontroller. Device 500 also comprises light-activated antimicrobial article 502 having viscoelastic layer 503 disposed on film backing 504. Photosensitizer is incorporated into the viscoelastic layer or is present as in a separate photosensitive layer (not shown) on top of the viscoelastic layer. If a photosensitive layer is used, then it may comprise photosensitizer with a woven or nonwoven cotton or rayon pad, silicon gel pad or a hydrogel pad. Light source 501 contacts the viscoelastic layer and the two are optically coupled such that light emitted by the light source can enter the viscoelastic layer. Similar devices could be useful as ostomy secural devices.

Film backing 504 comprises a backing that is conformable to anatomical surfaces. For example, the film backing may include an elastic film backing. The film backing may also comprise nonwoven fibrous webs, woven fibrous webs, knits and polymeric films which may be translucent and/or transparent. The film backing includes a layer of PSA (not shown) on top of the backing and which surrounds the viscoelastic layer and is ultimately used to adhere the article or device to the skin. Useful properties of an elastic film backing are described in U.S. Pat. No. 5,738,642 (Heinecke et al.) and references cited therein. For example, the elastic film backing needs to be moisture vapor permeable so that moisture vapor can be transmitted through the backing at an acceptable rate. Preferably, the moisture vapor transmission rate may be greater than or equal to skin. Exemplary elastic film backings have a PSA coated on polyurethane, polyester or polyether block amide films.

Light-activated antimicrobial article 502 may further comprise a release liner on top of the viscoelastic layer (or photosensitive layer) and that covers the exposed PSA layer of the film backing Light-activated antimicrobial article 502 may further comprise a carrier frame disposed on the film backing opposite the PSA layer. The carrier frame may be used to facilitate handling of the wound dressing. Wound dressings are described, for example, in U.S. Pat. No. 6,264,976 B1 (Heinecke et al.) and U.S. Pat. No. 5,738,642 (Heinecke et al.) and references cited therein. Similar devices may be useful as surgical incise drapes. Surgical incise drapes are described, for example, in U.S. Pat. No. 5,803,086 (Scholz et al.); U.S. Pat. No. 5,979,450 (Baker et al.) and U.S. Pat. No. 5,985,395 (Comstock et al.).

Figure 6:
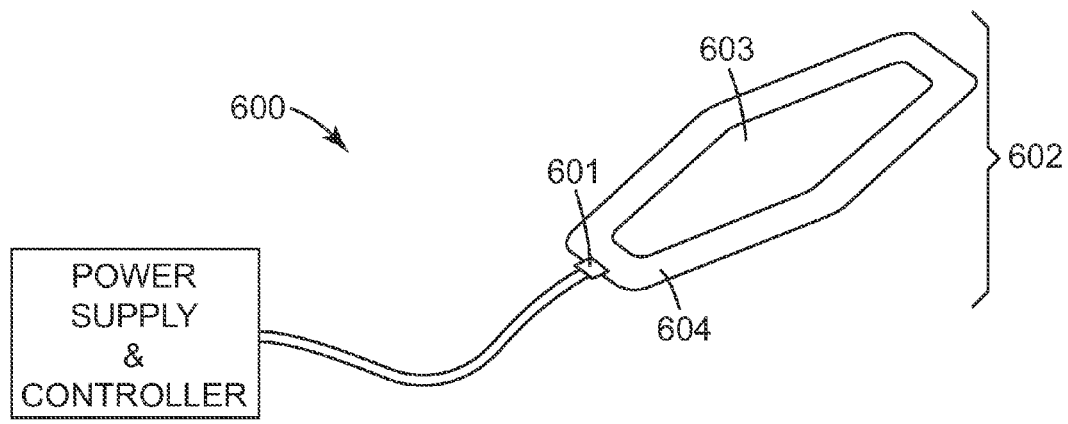

FIG. 6 shows a perspective view of exemplary light-activated antimicrobial device 600 which may be used as a wound dressing for light therapy. In this embodiment, device 600 comprises light source 601 electrically connected to a power supply with microcontroller. Device 600 also comprises light-activated antimicrobial article 602 having viscoelastic layer 603 disposed on film backing 604.

Photosensitizer is incorporated into the viscoelastic layer or is present as a separate layer (not shown) on top of the viscoelastic layer. Light source 601 contacts the PSA of the film backing such that the two are optically coupled. Light can be transported to the viscoelastic layer by the PSA of the film backing.

The embodiments shown in FIGS. 5 and 6 illustrate several useful variations of the article and device. For example, the viscoelastic material may be small or commensurate in size relative to that of the film backing. The viscoelastic layer and film backing may have the same shape or different shapes. For another example, the light source may be adjacent the viscoelastic material or the light source and viscoelastic material may be separated by a portion of the surface of the PSA of the film backing. In this case, the light source would be optically coupled to the PSA of the film backing.

The viscoelastic material may be made using any method or process commonly used for making viscoelastic articles. Typical processes comprise those that are continuous processes such as continuous cast and cure, extrusion, microreplication, and embossing methods. Various types of radiation may be used for processes in which a material needs to be cured, e.g., crosslinked. Various types of chemistries, including those that do not require radiation, may be used for materials that need to be cured. If the viscoelastic material is made from a curable material, then the material may be cured before, after or during contact with the light source. If the viscoelastic material is made from a cured material, then the material may be cured before, after or during contact with the substrate.

Conventional molding processes may also be used. Molds may be made by micro-machining, polishing or laser ablation of a mold material. Mold materials include polymeric, glass and metal materials. The molds may need to be suitable for making optically smooth surfaces of the viscoelastic material. The optically smooth surface of the viscoelastic material, if made from curable materials, may be formed by simply allowing the material to cure in air or other atmosphere such that the material levels itself.

Light-activated antimicrobial articles comprising the viscoelastic material and substrate may be made in a number of ways. In some embodiments, the material and substrate may be made separately, contacted and pressed together using finger pressure, a hand roller, an embosser or a laminator.

In some embodiments, the substrate may be formed on the viscoelastic material by coating a substrate material on the material. The substrate material may then be treated to form the substrate. For example, the substrate material may be extruded onto the viscoelastic material in the form of a layer and cooled to solidify the material to form the substrate. Alternatively, the substrate material may be curable and treated by heating and/or applying radiation to form the substrate. The substrate material may include solvent and the substrate is formed by removing the solvent.

In some embodiments, the viscoelastic material may be formed on the substrate by coating a viscoelastic material on the substrate. The viscoelastic material may then be treated to form the viscoelastic material. For example, the viscoelastic material may be extruded onto the substrate in the form of a layer and cooled to solidify the material to form the material. Alternatively, the viscoelastic material may be curable and treated by heating and/or applying radiation to form the material. The viscoelastic material may include solvent and the material is formed by removing the solvent.

In cases where the substrate material or the viscoelastic material is curable, an article having a partially cured substrate or material, respectively, may be made. In cases where the substrate material or the viscoelastic material is curable, chemically curing materials may be used such that the material is crosslinked. In cases where the substrate material or the viscoelastic material is curable, the material may be cured before, after and/or during contact with another material or the light source.

In cases where the substrate material or the viscoelastic material is curable using light, the light source may be optically coupled to the material and curing carried out by injecting light from the light source.

The light-activated antimicrobial articles and devices disclosed herein may be provided in any number of ways. The light-activated antimicrobial articles and devices may be provided as sheets or strips laid flat, or they can be rolled up to form a roll. The light-activated antimicrobial articles and devices may be packaged as single items, or in multiples, in sets, etc. The light-activated antimicrobial articles and devices may be provided in an assembled form, i.e., as part of some larger construction. The light-activated antimicrobial articles and devices may be provided as kits wherein the two are separate from each other and assembled at some point by the user. The light-activated antimicrobial articles and devices may also be provided separately such that they can be mixed and matched according to the needs of the user. The light-activated antimicrobial articles and devices may be temporarily or permanently assembled.

Also disclosed herein is a medical kit comprising: a light source, a viscoelastic material adapted to receive light from the light source, and a lotion comprising a photosensitizer that absorbs light that is received by the viscoelastic material.

The light-activated antimicrobial articles and devices disclosed herein may be used as part of a method for inhibiting the growth of microorganisms. A suitable method may comprise: providing a light source, providing a light-activated antimicrobial article comprising a photosensitizer and a viscoelastic material adapted to receive light from the light source, and coupling the light source and the photosensitizer such that the photosensitizer absorbs light from the viscoelastic material. Coupling the light source and the photosensitizer may comprise contacting the light source and the viscoelastic material. The light-activated antimicrobial article may be applied to the skin of a patient before or after the light source is coupled with the photosensitizer. The light-activated antimicrobial article may be exposed to a surface having a microorganism disposed thereon. The method may comprise activating the light source such that it emits light that is absorbed by the photosensitizer.

Another suitable method may comprise: providing a light source, providing a viscoelastic material adapted to receive light from the light source, applying a topical composition to the skin of a patient, the topical composition comprising a photosensitizer that absorbs light that is received by the viscoelastic material, contacting the topical composition on the skin of the patient with the viscoelastic material, and coupling the light source and the photosensitizer such that the photosensitizer absorbs light from the viscoelastic material.

The terms "in contact" and "disposed on" are used generally to describe that two items are adjacent one another such that the whole item can function as desired. This may mean that additional materials can be present between the adjacent items, as long as the item can function as desired.

EXAMPLES

An 8"×11" nylon nonwoven material was placed on top of a larger sheet of high grade optical poly(ethylene terephthalate) (PET) film. Then a 0.05 wt % aqueous solution of Acridine Yellow G was pipetted onto the nylon and another identical sheet of PET film was placed over the sample. Paper towels were placed underneath this construction and a roller was used to press the dye solution evenly throughout the nylon. Excess solution was roll-pressed away onto the paper towel. Once the solution was evenly distributed, the PET film was removed and the nylon sample was placed on clean paper towels and allowed to dry.

A PSA composition comprising 85/14/1 by weight of isooctyl acrylate/isobornyl acrylate/acrylic acid, 0.08 wt. % 1-6-hexanediol diacrylate and 0.20 wt. % IRGACURE 651 (Ciba Specialty) was coated onto a 4"×4" polymeric mirror film using a hand roller. The polymeric mirror film was a multilayer polymeric mirror film (Vikuiti™ ESR from 3M Co.). The thickness of the PSA layer was 40 mils (1000 um).

A release liner was placed over the PSA layer. A side-emitting LED was pressed into the PSA layer at one end, and when a 9V battery was connected to the LED, light easily passed through the entire length of the PSA layer.

The nylon samples were not sterilized prior to testing. Samples were cut in 2"×2" squares and placed on top of the release liner, which was not removed from the surface of the PSA layer. Each sample was inoculated with 1 ml of a suspension containing approximately $1-2\times10^5$ colony forming units (CFU)/m1 of an appropriate test organism. Inoculation was performed in the dark. Petri Dish covers were placed over the sample to prevent evaporation of the microbial suspension. Black insulating tape was taped over the LED-PSA junction to ensure all light emitted went through the PSA. The LED was then connected to a 9V battery. Samples were covered with aluminum foil to keep out extra light, and were incubated at 28° C. for 24 hours. After 24 hours incubation, each sample was separated from the release liner and placed in a sterile stomacher bag and 100 ml of D/E Neutralizing Broth was added. The sample was processed for one minute in a SEWARD Model 400 Stomacher. Serial dilutions of $10^0$, $10^1$ and up to $10^4$ were made and aerobic plate counts using 3M™ Petrifilm Aerobic Count (AC) were performed after incubating the Petrifilm plates at 37° C. for 48 hours.

Examples 1-5 as described in Table 1 were designed and tested as described above, except for the following changes:

Example 1 was a plain nylon sample without antimicrobial treatment that served as a control. It was incubated with a regular lamp installed in the incubator. It was not set up with the LED/PSA construction.

Example 2 was the Acridine Yellow G nylon. It was incubated with a regular lamp installed in the incubator. It was not set up with the LED/PSA construction.

Example 4 was a plain nylon sample without antimicrobial treatment that served as a control. It was incubated in the dark and was not set up with the LED/PSA construction.

Example 5 was the Acridine Yellow G nylon. It was incubated in the dark and was not set up with the LED/PSA construction.

Total colony forming units per sample were recorded after 48 hours of incubation at 35° C.±1° C. and the actual count was converted to log/cm². Samples were tested against *Staphylococcus aureus* (ATCC 6538).

TABLE 1

| Ex. | Description | CFU/cm² | Percent (%) Reduction |
|---|---|---|---|
| 3 | nylon/Acridine Yellow G (LED) | 5 | 99.99 |
| 2 | nylon/Acridine Yellow G (in regular light) | 5 | 99.99 |
| 5 | nylon/Acridine Yellow G (in dark) | 16,200 | 82.69 |
| 1 | plain nylon (in regular light) | 76,400 | NM |
| 4 | plain nylon (in dark) | 93,600 | NM |

What is claimed is:

1. A light-activated antimicrobial device comprising
   a light source, and
   a light-activated antimicrobial article comprising a photosensitizer and a layer of a pressure sensitive adhesive, wherein the pressure sensitive adhesive receives light from the light source into the layer through an end of the layer normal to a major surface of the layer, and manages the light such that the layer transports light through the length of the layer by total internal reflection, at least a portion of the light is absorbed by the photosensitizer.

2. The light-activated antimicrobial device of claim 1, wherein the photosensitizer is incorporated into the pressure sensitive adhesive, wherein greater than about 80% of the light received from the light source is absorbed by the photosensitizer.

3. The light-activated antimicrobial device of claim 1, the light-activated antimicrobial article comprising a photosensitive layer disposed on the pressure sensitive adhesive, the photosensitive layer comprising the photosensitizer, wherein the photosensitive layer extracts greater than about 80% of the light transported within the photosensitive pressure sensitive adhesive layer.

4. The light-activated antimicrobial device of claim 3, wherein the photosensitive layer comprises a fibrous material.

5. The light-activated antimicrobial device of claim 3, wherein the photosensitive layer comprises a polymeric material.

6. The light-activated antimicrobial device of claim 3, wherein the photosensitive layer comprises a membrane.

7. The light-activated antimicrobial device of claim 1, wherein the photosensitizer comprises a dye.

8. The light-activated antimicrobial device of claim 1, wherein the photosensitizer comprises a composition including:
   a catalyst that absorbs electromagnetic radiation and is selected from the group consisting of: metal oxides, metal sulfides, metal chalcogenites, metal phosphides, metal arsenides, non-metallic semiconductors, polymeric semiconductors, photoactive homopolyanions and photoactive heteropolyions;
   a solid that comprises anions that oxidize or react to generate a gas, the anions selected from the group consisting of chlorite, bisulfite, sulfite, hydrosulfide, sulfide, hypochlorite, cyanide and nitrate.

9. The light-activated antimicrobial device of claim 1, the light-activated antimicrobial article further comprising a substrate, wherein the pressure sensitive adhesive is disposed as a layer on the substrate.

10. The light-activated antimicrobial device of claim 9, wherein the substrate comprises an elastic film backing.

11. The light-activated antimicrobial device of claim 1, the light-activated antimicrobial article further comprising:
   a film backing, wherein the pressure sensitive adhesive is disposed as a viscoelastic layer on the backing and wherein at least a portion of the pressure sensitive adhesive layer comprises an optically smooth surface;
   a photosensitive layer disposed on the pressure sensitive adhesive layer opposite the backing; and
   a liner disposed on the photosensitive layer opposite the pressure sensitive adhesive layer.

12. The light-activated antimicrobial device of claim 11, wherein the film backing is an elastic film backing.

13. A light-activated antimicrobial article comprising a photosensitizer; a pressure sensitive adhesive layer adapted to receive light from a light source; and a substrate comprising an adhesive, the substrate disposed on the pressure sensitive adhesive layer, the substrate having a refractive index less than that of the pressure sensitive adhesive layer, wherein the pressure sensitive adhesive layer transports the light through the length of the pressure sensitive adhesive layer by total internal reflection such that at least a portion of the light is absorbed by the photosensitizer.

14. A method for inhibiting the growth of microorganisms, comprising
   providing a light source,
   providing a light-activated antimicrobial article comprising a photosensitizer and a layer of a pressure sensitive adhesive, the pressure sensitive adhesive adapted to receive light from the light source, and
   coupling the light source and the photosensitizer such that the pressure sensitive adhesive receives light into the layer through an end of the layer normal to a major surface of the layer, wherein the pressure sensitive adhesive manages the light received from the light source such that the layer transports light through the length of the layer by total internal reflection, the photosensitizer absorbs light from the pressure sensitive adhesive, and a reactive species is generated uniformly by the photosensitizer.

15. The method of claim 14, wherein coupling the light source and the photosensitizer comprises contacting the light source and the pressure sensitive adhesive.

16. The method of claim 14, wherein the light-activated antimicrobial article is applied to the skin of a patient before the light source is coupled with the photosensitizer.

17. The method of claim 14, wherein the light-activated antimicrobial article is applied to the skin of a patient after the light source is coupled with the photosensitizer.

18. The method of claim 14, further comprising
exposing the light-activated antimicrobial article to a surface having a microorganism disposed thereon.

19. The method of claim 14, further comprising activating the light source such that it emits light that is absorbed by the photosensitizer.

20. A light-activated antimicrobial device comprising
a light source, and
a light-activated antimicrobial article comprising a photosensitizer and a layer of a pressure sensitive adhesive, wherein the pressure sensitive adhesive receives light from the light source into the layer through an end of the layer normal to a major surface of the layer, and manages the light such that the layer transports light through the length of the layer by total internal reflection, at least a portion of the light is absorbed by the photosensitizer, wherein the photosensitizer is incorporated in discrete areas throughout pressure sensitive adhesive.

21. The light-activated antimicrobial device of claim 20, wherein the photosensitizer is incorporated as a gradient within the pressure sensitive adhesive.

\* \* \* \* \*